(12) United States Patent
Richter et al.

(10) Patent No.: US 7,030,108 B2
(45) Date of Patent: Apr. 18, 2006

(54) COMBATING PARKINSON'S DISEASE-RELATED MOVEMENT DISORDER

(75) Inventors: Virginia Pact Richter, Chapel Hill, NC (US); Thomas Giduz, Chapel Hill, NC (US)

(73) Assignees: Reed Richter, Chapel Hill, NC (US); Steven J. Hultquist, Raleigh, NC (US)

( * ) Notice: Subject to any disclaimer, the term of this patent is extended or adjusted under 35 U.S.C. 154(b) by 267 days.

(21) Appl. No.: 09/940,309

(22) Filed: Aug. 27, 2001

(65) Prior Publication Data

US 2002/0035057 A1    Mar. 21, 2002

Related U.S. Application Data

(63) Continuation of application No. 09/396,335, filed on Sep. 15, 1999, now Pat. No. 6,281,207.

(51) Int. Cl.
*A61K 31/55*    (2006.01)

(52) U.S. Cl. .................................. 514/214.02
(58) Field of Classification Search ............ 514/214.02
See application file for complete search history.

(56) References Cited

U.S. PATENT DOCUMENTS

| 3,983,234 | A | 9/1976 | Sayers ........................ 424/250 |
| 4,062,848 | A | 12/1977 | van der Burg ........ 260/268 PC |
| 4,968,692 | A | 11/1990 | Linnoila et al. ............. 514/396 |
| 5,198,459 | A | 3/1993 | Imperato et al. ............ 514/397 |
| 5,216,001 | A | 6/1993 | Perregaard et al. ......... 514/323 |
| 5,288,749 | A | 2/1994 | Meyer et al. ................ 514/414 |
| 5,948,806 | A | 9/1999 | Colpaert et al. ............. 514/397 |
| 6,281,207 | B1 | 8/2001 | Richter et al. ......... 514/214.02 |

FOREIGN PATENT DOCUMENTS

WO        WO 94/13285        6/1994

OTHER PUBLICATIONS

Henry et al., Experimental Neurology, 151(2), 334-342 (1998) (abstract).*
Rawlow et al., European Journal of Pharmacology, 191(3), 263-72 (1990) (abstract).*
Davis et al., CNS Drugs, 5/5 (389-402) (1996) (abstract).*
Lin-Shiau et al. Chemical Abstracts, vol. 121, Abstract No. 73678, 1994.

* cited by examiner

Primary Examiner—Phyllis G. Spivack
(74) Attorney, Agent, or Firm—Steven J. Hultquist; Intellectual Property/Technology Law

(57) ABSTRACT

A method of combating movement disorder is disclosed in a patient with Parkinson's disease comprising administering an effective amount of mirtazapine, a receptor antagonist for $5HT_{2/3}$ and $\alpha_2$ receptors.

14 Claims, No Drawings

COMBATING PARKINSON'S DISEASE-RELATED MOVEMENT DISORDER

CROSS-REFERENCE TO RELATED APPLICATION

This is a continuation of U.S. patent application No. 09/396,335 filed Sep. 15, 1999, and issued as U.S. Pat. No. 6,281,207 on Aug. 28, 2001.

BACKGROUND OF THE INVENTION

1. Field of the Invention

The present invention generally relates to the treatment of movement disorders in a patient suffering or susceptible to same, by administration to a patient of an effective amount of a neurotransmission modulating composition. More specifically, the invention relates to such treatment using a neurotransmission modulating composition comprising a 5HT- and/or $\alpha_2$ antagonist.

2. Description of the Related Art

Movement disorders include a wide variety of disease states and physiological conditions. Examples include various dyskinesias involving excessive or otherwise abnormal involuntary movement, which may vary significantly in rate, frequency, periodicity and progressionary character, and which may encompass disorders such as tremors, akathisias, asterixis, athetosis, choreaathetosis, tics, chorea/choreaform movements, dystonias, spasticity, restless legs syndrome, hyperkinetic movement disorders, hemiballismus, myoclonus, tardive dyskinesia and other types of dyskinesias.

Tremors types are particularly varied, and include for example Parkinsonian tremors, rubral tremors, post-traumatic tremors, drug-induced tremors (e.g. induced by lithium or other drug agents), cerebellar tremors associated with lesions of the cerebellum or cerebellar outflow pathway, Tourette syndromal tremors and other peripheral neuropathy-associated tremors.

These disorders, particularly dyskinetic conditions associated with neurological impairment of the basal ganglia, are far from uncommon in the general population. Approximately 1.5 million people are estimated to suffer from Parkinsonian tremor or essential tremor in the United States alone. The etiology of such physiologic states is poorly understood, involving striata comprising dopaminergic pathways whose transductional characteristics, neurotransmitter components and receptor mechanisms are ill-defined but constitute the focus of intensive research efforts directed to their elucidation.

Parkinson's tremor is a dyskinetic condition typically presenting as a resting tremor that is less pronounced, for example, when a person lifts his/her hand. Parkinson's tremor sometimes responds to L-DOPA, the classical treatment for the other symptoms of Parkinson's Disease (PD), but the tremor component is the most difficult symptom of the disease to treat effectively.

Levodopa-induced dyskinesias occur later in Parkinson's Disease and are extremely handicapping. Such dyskinesias range from subtle undulating movements of the body to wild uncontrollable swinging movements of the limbs that can literally knock a seated patient out of his or her chair and often makes it impossible for patients to feed themselves or perform other basic tasks requiring rudimentary manual dexterity and motor coordination.

Essential tremor and familial tremor are the same disease state in physiological manifestation, with familial tremor referring to the genetically-based incidence of such disease state. Essential tremor is the most common type of tremor; it can co-exist with PD tremor but is a categorically separate disease state.

Tremor is a pervasive movement disorder, for which few efficacious therapeutic agents presently exist, and there are many different types of this dyskinetic condition.

A concise overview of tremor varieties is located at the World Wide Web site http://www.geocities.com/~shaky-mtl/Newpage95.htm. Epidemiology charts for incidence of tremor are presented at the World Wide Web site http://www.geocities.com/~shaky-mtl/Newpage118.htm.

In the area of therapeutic compositions for treatment of movement disorders, there are few agents with demonstrated utility, and many of such agents have unacceptable side effect profiles.

Considering the therapeutic agents that have been used or proposed for treatment, beta-blockers such as Inderal have been used for essential tremor. Some secondary drugs are available, but they have generally poor efficacy. The mechanism of essential tremor is unknown and is probably not related to dopamine, since essential tremor does not respond to therapeutic agents that are generally used for treatment of Parkinson's Disease.

Recently, implantable electrodes in the brain have been used as a therapeutic intervention for Parkinson's tremor. This approach, however, is expensive and requires invasive techniques for placement in the basal ganglia and thalamus.

There is thus a compelling need in the art for efficacious therapeutic agents to treat movement disorders in all their variant forms.

SUMMARY OF THE INVENTION

The present invention generally relates to a method of combating movement disorder in a patient experiencing or susceptible to same, by administering to the patient an effective amount of a composition that is effective for combating such movement disorder.

In a specific aspect, the invention relates to a method of combating movement disorder in a patient experiencing or susceptible to same, by administering to the patient an effective amount of a neurotransmission modulating composition comprising a 5HT and/or $\alpha_2$ antagonist.

The composition in particular aspects may variously comprise:
  (a) a 5HT receptor antagonist, e.g., a 5HT2 and/or a 5HT3 receptor antagonist; and/or
  (b) an $\alpha_2$ receptor antagonist, e.g., a noradrenergic and serotonergic neurotransmission-enhancing/modulating agent.

In another aspect, the 5HT receptor antagonist (5HT2 and/or a 5HT3 receptor antagonist) may also be an $\alpha_2$ receptor antagonist.

Preferably, the antagonist composition is one that does not mediate sedation in dosages effective for combating movement disorder.

The various therapeutic compositions of the invention may additionally and optionally comprise any suitable adjuvants, excipients, additives, carriers, solvents, additional therapeutic agents (e.g., for conjoint treatment or therapy, including for example one or more additional agents for combating the movement disorder and/or a concurrent physiological condition), bioavailability enhancers, side-effect suppressing components, or other ingredients that do not preclude the efficacy of the composition for combating movement disorders.

Another aspect of the invention relates to a method of combating movement disorder in a patient experiencing or susceptible to same, comprising administering to the patient an effective amount of a piperazinoazepine compound that is a receptor antagonist for at least one receptor selected from the group consisting of 5HT and $\alpha_2$ receptors.

A further aspect of the invention relates to a method of combating movement disorder in a patient experiencing or susceptible to same, comprising administering to the patient an effective amount of a serotonergic antagonist for at least one receptor selected from the group consisting of 5HT and $\alpha_2$ receptors. For example, such serotonergic antagonist may be a 5HT2 and/or 5HT3 antagonist, and concurrently be an $\alpha_2$ receptor antagonist, e.g., a presynaptic $\alpha_2$ receptor antagonist and a post-synaptic 5HT receptor antagonist.

A further aspect of the invention relates to a method of combating movement disorder in a patient experiencing or susceptible to same, comprising administering to the patient an effective amount of mirtazapine.

Another aspect of the present invention provides the use of the active compound or composition in the preparation of a medicament for the treatment of movement disorder.

Other aspects of the invention relate to compositions of the above-mentioned types, as therapeutically formulated for combating movement disorder.

Still further aspects, features and embodiments of the invention will be more fully apparent from the ensuing disclosure and appended claims.

DETAILED DESCRIPTION OF THE INVENTION, AND PREFERRED EMBODIMENTS THEREOF

The present invention relates to method of combating movement disorder in a patient experiencing or susceptible to same, by administering to the patient an effective amount of a neurotransmission modulating composition comprising a 5HT antagonist and/or $\alpha_2$ antagonist.

The 5HT antagonist preferably includes at least one of 5HT2 antagonists and 5HT3 antagonists, but may be additionally or alternatively antagonistic at other 5HT subtype receptors. The composition may include a further $\alpha_2$ antagonist, with the 5HT antagonist and the $\alpha_2$ antagonist constituting the same or different compounds or compositional components.

The movement disorders to which the compositions of the invention are efficacious include movement disorders of all types, including dyskinesias of variant speed, rhythm, frequency and progressionary character.

For example, the movement disorder may comprise a condition selected from the group consisting of tremors, akathisias, asterixis, athetosis, choreaathetosis, tics, chorea/choreaform movements, dystonias, spasticity, restless legs syndrome, hyperkinetic movement disorders, hemiballismus, myoclonus, and tardive dyskinesia.

The method and compositions of the invention are effective in treatment of variant types of tremor, including peripheral neuropathy-associated tremor. The movement disorder that is treated by the method and compositions of the invention may for example comprise a tremor condition selected from the group consisting of Parkinsonian tremors, rubral tremors, post-traumatic tremors, drug-induced tremors, cerebellar tremors, and Tourette syndromal tremors.

The method and compositions of the invention are usefully employed in the treatment, prevention and amelioration of a wide variety of movement disorders deriving from neurological impairment of the basal ganglia, including for example Parkinsonian tremors, action tremors and levodopa-induced dyskinesias.

The neurotransmission modulating composition employed in the practice of the present invention may comprise any of a wide variety of 5HT antagonist and/or $\alpha_2$ antagonist agents. Useful agents include:
  (a) the compounds disclosed in U.S. Pat. No. 4,062,848 issued Dec. 13, 1977 to Willem Jacob van der Burg for "Tetracyclic Compounds," the disclosure of which is hereby incorporated herein by reference in its entirety;
  (b) imidazolines, e.g., phentolamine and tolazoline;
  (c) ergot alkaloids, e.g., ergotoxine and dihydrogenated peptide alkaloids;
  (d) indolealkylamine alkaloids, such as yohimbine;
  (e) compatible mixtures of at least one $\alpha_2$ antagonist in combination with at least one 5-hydroxytryptamine (e.g., 5HT2 and/or 5HT3) receptor antagonist.

The therapeutic composition of the invention may comprise compatible mixtures of at least one $\alpha_2$ antagonist in combination with at least one 5-hydroxytryptamine (e.g., 5HT2 and/or 5HT3) receptor antagonist. Suitable $\alpha_2$ antagonists may for example include atipamezole, idazoxan, and imiloxan, as well as other alpha-2 adrenoceptor antagonist compounds described in U.S. Pat. No. 4,968,692 issued Nov. 6, 1990 to Markku Linnoila, et al., and the tertiary and secondary amines disclosed in U.S. Pat. No. 5,288,749 issued Feb. 22, 1994 to Michael D. Meyer, et al., including, for example, N-(2-(N-Methanesulfonamido-2,3-dihydroindol-5-yl)ethyl) (-N-((R)-(+)-5-methoxy-1,2,3,4-tetrahydronapbthalen-1-ylmethyl)-N-methylamine;

N-(2,3-Dihydroindol-5-yl)ethyl(-N-((R)-(+)-5-methoxy-1,2,3,4-tetrahydronaphthalen-1-ylmethyl)-N-methylamine, N-(2-(N-Methanesulfonamido-2,3-dihydroindol-6-yl)ethyl (-N-((R)-(+)-5-methoxy-1,2,3,4-tetrahydronaphthalen-1-ylmethyl)-N-methylamine;

N-(2-(N-Propanesulfonamido-2,3-dihydroindol-6-yl)ethyl(-N-((R)-(+)-5-methoxy-1,2,3,4-tetrahydronaphthalen-1-ylmethyl)-N-methylamine;

N-(2-(N-Isobutanesulfonamido-2,3-dihydroindol-6-yl)ethyl (-N-((R)-(+)-5-methoxy-1,2,3,4-tetrahydronaphthalen-1-ylmethyl)-N-methylamine;

N-(2-(N-Methyl-2,3-dihydroindol-5-yl)ethyl(-N-((R)-(+)-5-methoxy-1,2,3,4-tetrahydro-naphthalen-1-yl)-N-methylamine;

N-(2-(N-Methyl-2,3-dihydroindol-6-yl)ethyl(-N-((R)-(+)-5-methoxy-1,2,3,4-tetrahydro-naphthalen-1-ylmethyl)-N-methylamine;

N-(2-(2,3-Dihydroindol-6-yl)ethyl(-N-((R)-(+)-5-methoxy-1,2,3,4-tetrahydronaphthalen-1-ylmethyl)-N-methylamine;

N-(2-(2,3-Dihydroindol-5-yl)ethyl(-N-((R)-(+)-5-methoxy-1,2,3,4-tetrahydronaphthalen-1-ylmethyl)-N-methylamine;

N-(2-(Indol-6-yl)ethyl(-N-((R)-(+)-5-methoxy-1,2,3,4-tetrahydronaphthalen-1-yl)methyl)-N-methylamine;

N-(2-(N-Methanesulfondamido-1,3-dihydroisoindol-5-yl) ethyl(-N-((R)-(+)-5-methoxy-1,2,3,4-tetrahydronaphthalen-1-ylmethyl)-N-methylamine;

N-(2-(N-Methyl-1,3-dihydroisoindol-5-yl)ethyl(-N-((R)-(+)-5-methoxy-1,2,3,4-tetrahydronaphthalen-1-ylmethyl)-N-methylamine;

N-(2-(1,3-Dihydroisoindol-5-yl)ethyl(-N-((R)-(+)-5-methoxy-1,2,3,4-tetrahydronaphthalen-1-ylmethyl)-N-methylamine;

N-(2-(N-Methyl-2,3-dihydro-1H-indol-5-yl)-ethyl(-N-((R)-(+)-5-methoxy-1,2,3,4-tetrahydronaphthalen-1-ylmethyl)-N-methylamine; and 5- {2-(((R)-(+)-5-Methoxy-1,2,3,4-tetrahydro-naphthalen-1-ylmethyl)methylamino)-ethyl}-1,3-dihydro-indol-2-one, while suitable 5HT (e.g., 5HT2 and/or 5HT3) antagonists include ergonovine (Ergotrate), pizotifen, mianserin, Ketanserin (Sufrexal), Ondansetron (Zofran), ritanserin, clozapine (Clozaril), risperidone (Risperdal), methysergide (Sansert), and cyproheptadine (Periactin), as well as the compounds disclosed in U.S. Pat. No. 5,198,459 issued Mar. 30, 1993 to Assunta Imperato, et al., including, for example, indol-3-yl-carboxylic acid-endo-8-methyl-8-aza-bicyclo[3,2,1]-oct-3-yl-ester;

benzo[b]thiophen-3-yl-carboxylic acid-endo-9-methyl-azabicyclo-[3,3,1]non-3-yl-ester;

5-fluoro-1-methyl-indol-3-yl-carboxylic acid-endo-9-methyl-9-aza-bicyclo[3,3,1]non-3-yl-ester;

1,2,3,9-tetrahydro-9-methyl-3-[(2-methyl-1H-imidazol-1-yl)-methyl-4H-carbaz ol-4-one;

1-methyl-indazol-3-yl-carboxylic acid-9-methyl-9-aza-bicyclo-[3,3,1]-non-3.alpha.-yl-amide;

endo-4-amino-5-chloro-2-methoxy-N-(1-azabicyclo[3,3,1] non-4-yl)-benzamide; and

3-[5-methyl-1H-imidazol-4-yl]-1-(1-methyl-1H-indol-3-yl)-1-propanone.

One class of compounds that may be usefully employed as tremor-combating agents in accordance with the present invention include the tetracyclic compounds of U.S. Pat. No. 4,062,848, of the formula:

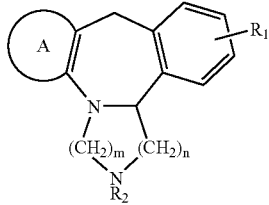

or a salt thereof, wherein

A represents a pyridine ring or a halogen substituted pyridine ring, $R_1$ represents hydrogen, $C_1$–$C_6$ alkyl, $C_1$–$C_6$ alkoxy, $C_1$–$C_6$ alkylthio, halogen, OH, SH or $CF_3$ $R_2$ represents hydrogen or a lower alkyl or aralkyl group and n and m may each be 1, 2 or 3 with the proviso that the sum of m and n must be 2, 3 or 4.

Various other presynaptic alpha-2 receptor antagonists and 5-HT2 and 5-HT3 postsynaptic receptor antagonists may likewise be employed in the treatment of movement disorder in the broad practice of the present invention.

One presently preferred movement disorder-combating therapeutic composition in the general practice of the present invention comprises mirtazapine, a piperazinoazepine characterized as (i) a presynaptic alpha-2 antagonist that acts to increase noradrenergic and serotonergic neurotranmission, and (ii) a postsynaptic serotonergic 5-HT2 and 5-HT3 antagonist. Mirtazapine, or 6-azamianserin, includes the compound, 1,2,3,4,10,14b-hexahydro-2-methyl-pyrazino [2,1-a]pyrido [2,3-c]benzazepine) in racemic forms. The S(+) enantiomer has the formula:

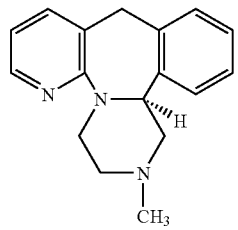

Mirtazapine is sold in racemic mixture under the trademark REMERON (NV Organon, Oss, The Netherlands) as an FDA-approved drug for the treatment of depression, for which indication the usual daily dose is on the order of from about 15 to about 60 milligrams (mg.). The present invention contemplates the use of the racemic mixture mirtazapine, as well as the use of substantially pure enantiomeric components thereof, e.g., produced by chiral synthesis or by appropriate racemic separation technique, as well as the use of non-racemic mixtures of the respective D- and L-racemic forms.

While we do not wish to be bound by any theory or hypothesis as to the mode or mechanism of activity of 5HT antagonist and/or $\alpha_2$ antagonist agents in the treatment of movement disorder in the broad practice of the present invention, it is known that the presently preferred mirtazepine composition functions to enhance both noradrenergic and serotonergic neurotransmission, acting presynaptically as an $\alpha_2$ antagonist which disinhibits both NE and 5HT neurons, thereby increasing levels of NE and 5HT in the brain. Serotonin is directed to the 5HT1A receptor while the mirtazepine composition inhibits 5HT2 and 5HT3 receptors. Other movement disorder-combating compositions within the broad scope of the present invention may act in an analogous manner.

Patients treated with compositions in accordance with the invention, as hereinafter more fully described, experienced clinically significant relief of their symptoms without sedation.

In patients experiencing remission of movement disorder symptoms incident to the administration of dyskinesia-combating compositions of the present invention, marked improvement is typically noted within 24 hours at relatively low doses (15–30 mg). In general, the dosage range may be suitably varied as required for efficacy, and the specific dosage of compositions within the broad scope of the present invention may be readily determined without undue experimentation, in a quick and simple manner, particularly in view of the contemporaneously manifested efficacy at appropriate therapeutic dosage.

For example, the preferred mirtazapine composition may be administered to a human patient at a daily dose in the range of from about 10 to about 100 milligrams, and more preferably from about 15 to about 50 milligrams. Such dosage may be administered in a single or multiple dosage form, e.g., an oral tablet or capsule.

More generally, and with reference herein to specific compounds or classes of compounds as usefully employed in the practice of the invention, such compounds or classes of compounds are intended to be broadly construed to encompass within the scope thereof salts, esters, amides, carbamates, solvates, polymorphs, hydrates, affinity reagents, tautomeric forms, optical isomers that are either dextrorotatory or levorotatory, respective dextrorotatory or levorotatory pure preparations, and mixtures thereof, stereoisomers (enantiomers and diastereoisomers) and mixtures thereof, derivatives and/or prodrugs of such compounds, in either crystalline or amorphous form. The esters, amides and carbamates are preferably hydrolyzable and are more preferably biohydrolyzable. The salts are preferably pharmaceutically acceptable salts.

The movement disorder-combating compounds described herein may also be substituted by substituents which are sterically acceptable, chemically and biochemically compatible and which do not preclude the efficacy of the compound for its intended utility of combating a movement disorder condition. In enantiomeric forms, compounds of the invention include individual enantiomers of the compounds in single species form substantially free of the corresponding enantiomer, as well as in admixture (in mixtures of enantiomeric pairs and/or in mixtures of multiple enantiomer species).

Pharmaceutically acceptable esters of movement disorder-combating compounds of the invention include carboxylic acid esters of hydroxy groups in such compounds in which the non-carbonyl moiety of the carboxylic acid portion of the ester grouping is selected from straight or branched chain alkyl (e.g. n-propyl, t-butyl, n-butyl), alkoxyalkyl (e.g. methoxymethyl), arylalkyl (e.g. benzyl), aryloxyalky (e.g. phenoxymethyl), and aryl (e.g. phenyl); alkyl-, aryl-, or arylalkylsulfonyl (e.g. methanesulfonyl); amino acid esters (e.g. L-valyl or L-isoleucyl); dicarboxylic acid esters (e.g. hemisuccinate); carbonate esters (e.g. ethoxycarbonyl); carbamate esters (e.g. dimethylaminocarbonyl, (2-aminoethyl)aminocarbonyl); and inorganic esters (e.g. mono-, di- or triphosphate).

Pharmaceutically acceptable salts of the movement disorder-combating compounds of the invention and physiologically functional derivatives thereof include salts derived from an appropriate base, such as an alkali metal (for example, sodium, potassium), an alkaline earth metal (for example, calcium, magnesium), ammonium and $NX_4^+$ (wherein X is $C_1$–$C_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxy group consist of the anion of said compound in combination with a suitable cation such as Na+, $NH_4^+$ or $NX_4^+$ (wherein X is for example a $C_{1-4}$ alkyl group).

For therapeutic use, salts of movement disorder-combating compounds of the invention will be pharmaceutically acceptable, i.e., they will be salts derived from a pharmaceutically acceptable acid or base. However, salts of acids or bases which are not pharmaceutically acceptable may also find use, for example, in the preparation or purification of a pharmaceutically acceptable compound. All salts, whether or not derived from a pharmaceutically acceptable acid or base, are within the scope of the present invention.

Subjects to be treated by the methods of the present invention include both human and non-human animal (e.g., bird, dog, cat, cow, horse) subjects, and are preferably mammalian subjects, and most preferably human subjects.

Depending on the specific movement disorder to be treated, animal subjects may be administered compounds and compositions of the invention at any suitable therapeutically effective and safe dosage, as may readily be determined within the skill of the art, and without undue experimentation.

In general, while the effective dosage of compounds of the invention for therapeutic use may be widely varied in the broad practice of the invention, depending on the specific application, dyskinetic condition, or physiological state involved, as readily determinable within the skill of the art, suitable therapeutic doses of the compounds and compositions described herein, and for achievement of therapeutic benefit in treatment, will broadly be in the range of 10 micrograms (μg) to 100 milligrams (mg) per kilogram body weight of the recipient per day, preferably in the range of 50 μg to 75 mg per kilogram body weight per day, and most preferably in the range of 100 μg to 50 mg per kilogram body weight per day. The desired dose may be presented as one, two, three, four, five, six, or more sub-dose(s) administered at appropriate intervals throughout the day, or alternatively in a single dose at morning or evening administration. These sub-doses may be administered in unit dosage forms, for example, containing from 10 μg to 200 mg, preferably from 50 μg to 100 mg, more preferably from 50 μg to 250 mg, and most preferably from 50 μg to 50 mg of active ingredient per unit dosage form. Alternatively, if the condition of the recipient so requires, the doses may be administered as a continuous infusion.

The mode of administration and dosage forms will of course affect the therapeutic amounts of the compounds or compositions which are desirable and efficacious for the given treatment application.

For example, orally administered dosages typically are at least twice, e.g., 2–10 times, the dosage levels used in parenteral administration methods, for the same active ingredient. In oral administration, dosage levels for movement disorder-combating compounds of the invention may be on the order of 5–200 mg/70 kg body weight/day. In tablet dosage forms, typical active agent dose levels are on the order of 10–100 mg per tablet.

The movement disorder-combating compounds or compositions may be administered per se as well as in the form of pharmaceutically acceptable ethers, esters, salts, and other physiologically functional derivatives thereof.

The present invention also contemplates pharmaceutical formulations, both for veterinary and for human medical use, which comprise as the active agent one or more compound(s) or composition(s) of the invention.

In such pharmaceutical formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterine administration. Formulations suitable for oral administration are preferred.

When the active agent is utilized in a formulation comprising a liquid solution, the formulation advantageously may be administered orally or parenterally. When the active agent is employed in a liquid suspension formulation or as a powder in a biocompatible carrier formulation, the formulation may be advantageously administered orally, rectally, or bronchially.

When the active agent is utilized directly in the form of a powdered solid, the active agent may advantageously administered orally. Alternatively, it may be administered bronchially, via nebulization of the powder in a carrier gas, to form a gaseous dispersion of the powder which is inspired by the patient from a breathing circuit comprising a suitable nebulizer device.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The formulations comprising the active agent of the present invention may conveniently be presented in unit dosage forms and may be prepared by any of the methods well known in the art of pharmacy. Such methods generally include the step of bringing the active compound(s) into association with a carrier that constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of delivery and target location of the body. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal spray formulations comprise purified aqueous solutions of the active compounds with preservative agents and isotonic agents. Such formulations are preferably adjusted to a pH and isotonic state compatible with the nasal mucous membranes. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

The features and advantages of the invention are more fully shown by the following non-limiting examples.

EXAMPLE 1

A 73 year-old female patient with mild Parkinson's Disease for 4 years experienced recurrent tremor that interfered with her ability to hold and deal cards while playing bridge. The patient had mild bradykinesia and slow Parkinsonian gait that was treated and completely relieved with Sinemet. She continued to experience a resting and action tremor. The patient was administered mirtazapine (Remeron®, Organon) at a dosage of 30 mg per day, taken at night for concomitant depression. The patient reported that within days of initial administration of mirtazapine, she could hold her cards without embarrassment.

Two months later, the patient discontinued the administration of mirtazapine because she was oversleeping. Such oversleeping behavior was not believed to relate to the administration of mirtazapine, however. The patient in fact stopped and restarted the mirtazapine multiple times. Upon cessation of such medication, the tremor (resting and action) returned. The administration of mirtazapine was thereupon reinitiated and the patient again experienced resolution of the tremors. Throughout the above-described initial administration of mirtazapine, cessation of such medication, and its subsequent resumption of administration, the dosage of Sinemet did not change. The patient currently remains on mirtazapine without experiencing any sedation side effect.

EXAMPLE 2

A 56 year old male with a 15 year history of Parkinson's Disease was treated. When first seen in 1990 for treatment, he exhibited left upper extremity resting tremor and bradykinesia which responded to treatment with prescribed Sinemet and dopa agonists. By 1996, on/off phenomenon and violent dyskinesias greatly increased his disability. In August, 1997, the patient was started on mirtazapine (Remeron) at a dosage of 3 mg at night to aid in sleep. The next morning the patient's spouse telephoned excitedly to say that the spouse had only shaken for 15 minutes. This positive development continued making his "on" time more functional. The patient never reported that he was drowsy during the day.

Six months later, when a new dopa agonist (ropirinole) was added to the patient's medication, there was no increase in dopamine-induced dyskinesias. Throughout the regimen of treatment, the dose of Sinemet remained stable.

EXAMPLE 3

A 72 year old female with a nine-year history of Parkinson's Disease characterized by bradykinesia and marked right upper extremity resting tremor was treated. All aspects of the disease were well controlled with Sinemet and dopa agonists except the tremor.

After seven years of treatment, the patient developed pronounced dopamine-induced dyskinesias. Some control was achieved by lowering the dose of Sinemet. In May 1998, she was started on mirtazapine (Remeron) at a dosage of 30 mg at night. The patient reported rapid improvement in the dyskinesias and the Parkinsonian tremor. No other medication had been changed.

Several months later the patient stopped the mirtazapine (Remeron) medication and noted return of the tremor and dyskinesia. Upon restarting the mirtazapine (Remeron), both movement disorders again responded and the previously seen improvement was again experienced.

EXAMPLE 4

A 76 year old female with a 20-year history of upper extremity action tremor with a frequency of approximately 8–12 hz. The patient bad no signs or symptoms of Parkinson's disease. Her tremor was not well controlled on Mysoline. The patient was started on mirtazapine (Remeron) at a dosage of 30 mg at night. On physical exam, the patient's postural and kinetic tremors were greatly reduced and she had decreased her dose of Mysoline on her own to one tablet a day.

EXAMPLE 5

A 76 year old female with a lifelong history of action tremor and anxiety but no signs or symptoms of Parkinson's disease was treated. The tremor seemed to respond to propranolol initially though the tremor clearly was related in severity to the state of the anxiety disorder. Although the tremor always improved with a decrease in the anxiety (using SSRIs and benzodiazepines) the tremor persisted at an unsatisfactory level of severity.

In March, 1998, the patient began medication with a dosage of 15 mg of mirtazapine (Remeron) at night, then on her own volition, increased the administration of the same dose of mirtazapine to twice a day (for a total dose of 30 mg). The patient reported improvement in the tremor especially when eating or drinking, though her handwriting remained a problem. The clinical exam improved marginally, but functionally, the patient felt better and chose to remain on the mirtazapine medication.

EXAMPLE 6

Subsequent to study of the patients described in Examples 1–5, ten additional patients were treated with mirtazapine for tremor, and seven of these patients responded favorably with marked attenuation of tremor activity.

Thus, in the patient group involved in the study of Examples 1–6, a total of fifteen individuals was treated with mirtazapine, and of such population, twelve of the patients responded well to treatment with substantial tremor reduction. Of such total of fifteen patients, eight patients had essential tremor, and five of the eight responded. Four patients had a Parkinsonian resting tremor and three patients responded (the fourth patient has recently begun treatment and has not yet returned for follow-up). Three patients had levodopa-induced dyskinesias and all three responded.

In almost all cases, the improvement in the tremor behavior came literally overnight, that is, after an initial 30 mg dose taken in the evening before retiring. Sedation can improve certain types of tremor but sedation did not occur in the above-referenced examples. Patients were aware of an improvement immediately. During neurological exam, patients described the types of activities that they could perform before and after administration of mirtazapine (e.g., dealing cards, feeding oneself without spilling, being able to return to exercise classes as a consequence of the improvement experienced, etc.).

All patients in whom it has been effective continue to take mirtazapine to the present time, in some instances for a period of two years. Some patients in the above-identified tests, many of whom had other complex medical problems, took the mirtazapine sporadically or in response to worsening of symptoms subsequent to discontinuing such medication.

Although the invention has been variously disclosed herein with reference to illustrative aspects, embodiments and features, it will be appreciated that the aspects, embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A method of combating Parkinson's disease-related movement disorder in a patient experiencing or susceptible to same who is being treated with dopaminergic medication, anticonvulsant medication or antianxiolytic medication, said method comprising administering to the patient an effective amount of mirtazapine.

2. The method of claim 1, wherein said patient is being treated with dopaminergic medication.

3. The method of claim 2, wherein said dopaminergic medication comprises a dopa agonist.

4. The method of claim 2, wherein said dopaminergic medication comprises medication selected from the group consisting of (i) levodopa, (ii) levodopa in combination with carbidopa, and (iii) ropirinole.

5. The method of claim 1, wherein said patient is being treated with anticonvulsant medication.

6. The method of claim 5, wherein said anticonvulsant medication comprises primidone.

7. The method of claim 1, wherein said movement disorder comprises bradykinesia.

8. The method of claim 1, wherein said movement disorder comprises resting tremor.

9. The method of claim 1, wherein said movement disorder comprises tremor.

10. The method of claim 1, wherein said movement disorder comprises action tremor.

11. The method of claim 1, wherein said patient is being treated with anxiolytic medication.

12. The method of claim 11, wherein said anxiolytic medication comprises propranolol.

13. The method of claim 11, wherein said anxiolytic medication comprises an SSRI.

14. The method of claim 11, wherein said anxiolytic medication comprises a benzodiazapine.

* * * * *